United States Patent [19]

Landau

[11] Patent Number: 4,592,742

[45] Date of Patent: Jun. 3, 1986

[54] PRESSURE HYPODERMIC SYRINGE

[76] Inventor: Sergio Landau, Av. Epitácio Pessao, no. 2870/202, Lagoa-Rio de Janeiro, Brazil, CEP.22471

[21] Appl. No.: 709,127

[22] Filed: Mar. 7, 1985

[30] Foreign Application Priority Data

Aug. 28, 1984 [BR] Brazil .................................. 8404286

[51] Int. Cl.⁴ ............................................. A61M 5/30
[52] U.S. Cl. ..................................................... 604/71
[58] Field of Search ..................... 604/71, 70, 69, 68, 604/234, 232

[56] References Cited

U.S. PATENT DOCUMENTS

| | | | |
|---|---|---|---|
| 3,129,708 | 4/1964 | Krantz | 604/68 |
| 3,334,788 | 8/1967 | Hamilton | 604/135 |
| 3,526,225 | 9/1970 | Isobe | 604/71 |
| 4,103,684 | 8/1978 | Ismach | 604/71 |
| 4,342,310 | 8/1982 | Lindmayer et al. | 604/71 |
| 4,368,731 | 1/1983 | Schramm | 604/234 |

Primary Examiner—John D. Yasko
Attorney, Agent, or Firm—Anthony A. O'Brien

[57] ABSTRACT

A pressure hypodermic syringe designed to inject liquid medication includes the feature of simultaneously utilizing a pressure injection system and of comprising basically the two elements that characterize each and every syringe using conventional hypodermic needles, that is, a transparent graded cylinder where the desired medication dose is inserted, and a piston for intake and injection of the dose by displacing itself inside the transparent graded cylinder. The present invention is characterized by being the only hypodermic injection device to dispense with the use of needles while at the same time retaining the simplicity and safely qualities of conventional syringes, since the user may visually set the desired dose for injection and check for the presence of air bubbles before each injection.

9 Claims, 6 Drawing Figures

PRESSURE HYPODERMIC SYRINGE

This invention refers to a pressure hypodermic syringe designed to inject intradermal, subcutaneous or intramuscular liquid medication, in which rather than the conventional hypodermic needle the tip contains only a small orifice that comes in direct contact with the skin of the person who is to receive a dose of the medication to be injected. The syringe has the unique property of simultaneously utilizing the pressure injection method and of having only the two basic components which make up any conventional hypodermic needle syringe, i.e. a transparent and graded cylinder where the desired medication dose is inserted, and a piston for intake and injection of said dose by moving inside the transparent and graded cylinder. Thus the present invention is the only hypodermic injection device to preclude the use of needles while retaining the same simple and safe features of a common syringe, since the user may visually adjust the desired dose for injection as well as check for air bubbles prior to injection.

The needleless pressure injection method is widely known and its efficacy has been proven in several countries throughout many years of practical application. The method consists basically of the introduction of a given amount of medication in the intradermal, subcutaneous or intramuscular tissues of persons or animals by way of a small orifice pressed against the skin, through which the medication is passed at high speed with the aid of a pressure mechanism, usually a spring, a hydraulic system or capsules containing gases under pressure.

Over the last three decades, a number of hypodermic needleless devices has been invented for injection of medication under pressure. Such devices have been generically named "pressure hypodermic injectors" or "jet hypodermic injectors". The designers of said devices have basically tried to achieve either of the two objectives below:

(a) To make hypodermic injections more comfortable and less painful for the recipient.
(b) To provide a faster and more practical method of preparation and application of the hypodermic injection.

Interest was first drawn to devices for hypodermic application of vaccines. Large-size, complex and usually hydraulically-driven pistols were used by trained vaccinators mainly for mass vaccination campaigns.

Later the pressure injection method was extended to vaccines and medication injected at fixed and smaller doses. It was found then that in such cases smaller, mechanically- and manually-operated injection applicators could be handled by the technician in charge. Devices of this type then became commonly used in dental offices, in dermatology, plastic surgery, allergy clinics and public health centers, the latter for application of certain types of vaccines. However, application was generally performed by specialists in each field and always limited to fixed and very small doses.

Finally, consideration was given the fact that hypodermic injections are not always administered by physicians, nurses, vaccinators or pharmacists. Sometimes the injection is applied by the patient or a member of his/her family. A typical example of this are diabetics who must have daily injections of insulin to survive. Diabetics in general have a regular syringe at home which is kept sterilized and is used for self-application. Such persons often resort to disposable syringes.

To reach that market, some inventors have attempted to devise smaller hypodermic pressure injectors of variable dose and manual application.

Although some such devices have been introduced in the market lately, they have not gained wide acceptance by diabetics.

The poor acceptance is due to the fact that, although considerably smaller than the earlier pressure injectors, they differ greatly from the common hypodermic syringe in that they require greater handling skill, are not considered reliable by the users who cannot visualize what happens to the medication inside the syringe, and finally are not very practical, in addition to being overly expensive for regular non-professional use, that is, for individual use by the patient.

Therefore, the common hypodermic syringe is still massively utilized by diabetics for subcutaneous insulin injections.

Although the common glass or disposable hypodermic syringe involves the trauma and discomfort of the "pinprick", it is still widely used because it remains the simplest and safest device available in the market for hypodermic injection of desired doses of insulin.

The rationale behind the present invention has been precisely to provide an alternative to the conventional hypodermic syringe which might retain its two basic qualities of safety and simplicity while removing the physical aggression caused by the hypodermic needle.

In short, the new syringe would meet the needs of people who fear or suffer from the use of hypodermic needles although heavily dependent on frequent injection of hypodermic medication at accurate and varying doses, such as insulin. Those individuals, often children, teenagers and mothers who administer insulin to small children, would like to avoid the needle prick without losing the two qualities of common hypodermic syringes, i.e. simplicity and assurance of accurate control of the desired dose of the medication applied.

Design of this new syringe therefore must aim at the simplicity and safety of a conventional hypodermic syringe while providing the means to inject variable doses of liquid medication under pressure and without the aid of a needle.

Design details and operation of the invention will be discussed in the attached set of drawings.

Figure 1:
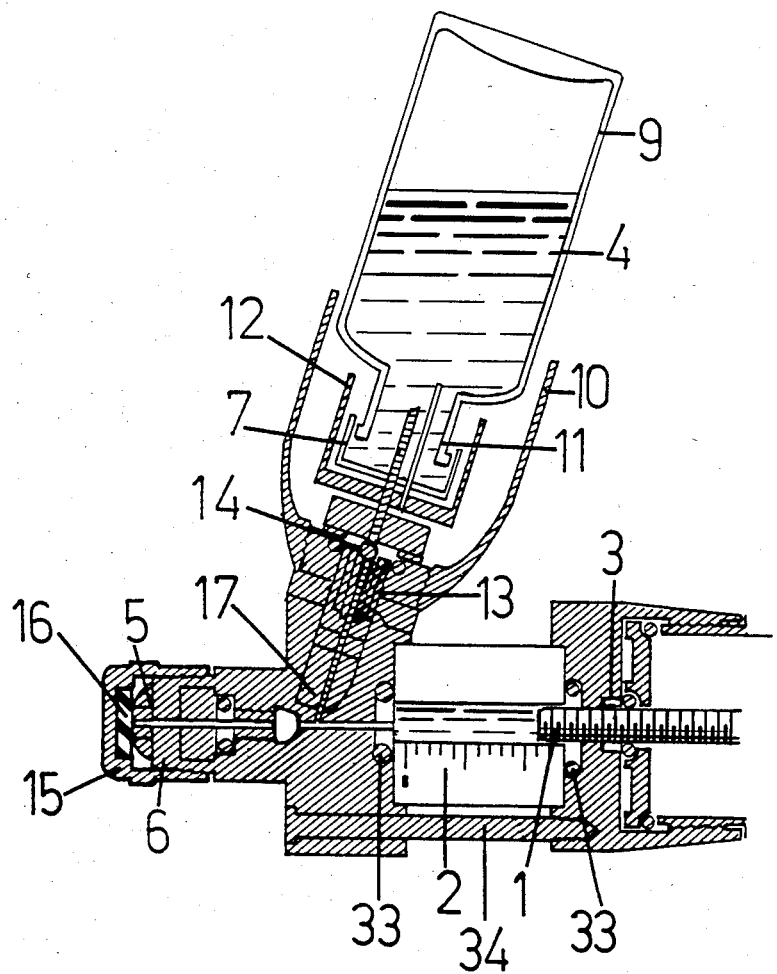
FIG. 1 (one) shows a cross-section of the front part of the pressure hypodermic syringe with the medication dose inside the transparent and graded injection cylinder.
Figure 2:
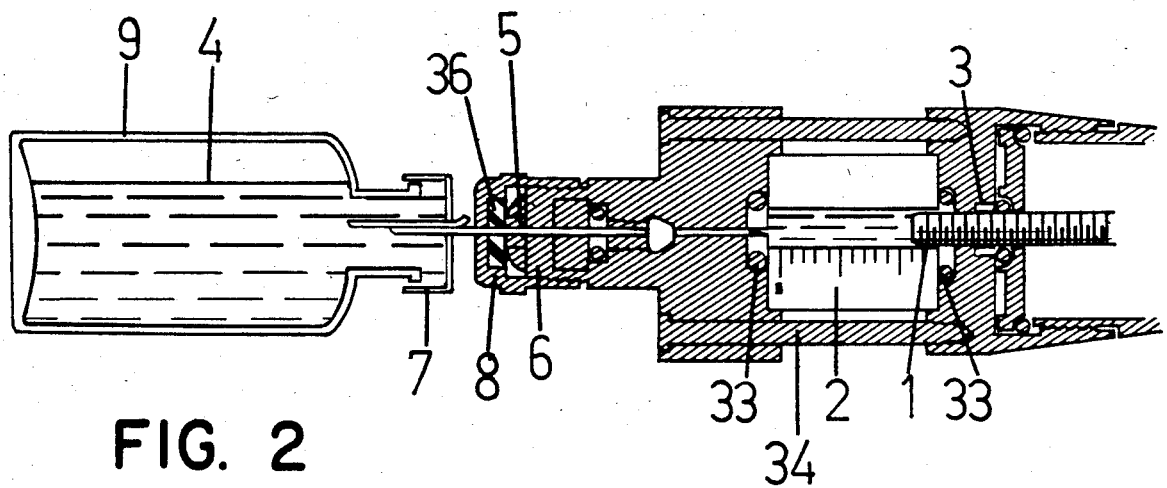
FIG. 2 (two) is a cross-section of the front part of a simplified pressure hypodermic syringe that does not require either a vial holder or valve, but utilizes instead an adapter to draw the medication into the syringe.

FIG. 1 clearly shows the operational system of the pressure hypodermic syringe to be very similar to that of any conventional hypodermic syringe, that is, an injection piston (1) slides forward and back inside a transparent graded injection cylinder causing intake and injection of a set volume of liquid. Since the piston (1) is sealed to the injection cylinder (2) at its back end through a sealing ring (3), the liquid or medication to be injected (4) will necessarily have to enter and exit the injection cylinder (2) through the front end.

In a conventional syringe, the drug enters the transparent injection cylinder through the same hypodermic needle that will inject the liquid. In other words, the liquid enters and exits through the same port.

In the pressure hypodermic syringe the volume of liquid found in the transparent injection cylinder (2) always exits through the front orifice (5) located in the injection nozzle (6), when the injection piston (1) pushes in that direction. However, the same volume of liquid may enter the transparent injection cylinder (2) in two different ways.

The path followed by the medication dose in the simplified version of the pressure hypodermic syringe will be shown next through FIG. (2).

The adaptor needle (7) is passed through the sealing rubber lid of the medication vial (9). The needle has two cannulas lying side by side. While one cannula pierces the adaptor exactly at midpoint, the second cannula (11) does not. It ends just short of the adaptor, with one of its tips slightly bent.

As the needle (7) and its two cannulas move through the rubber lid of the medication vial (9), the entire set of bottle-adaptor is screwed to the pressure hypodermic syringe injection nozzle (6). Thus the front orifice (5) is aligned to the central cannula of the adaptor (8) needle (7) by contact with a sealing disc (36) with a central orifice.

When the injection piston (1) is pulled back, vacuum is generated inside the needle (7)-injection nozzle (6)-injection cylinder (2) path, since the path is completely sealed against air intake. So the medication can be drawn in by the motion of the injection piston (1) and deposited in the transparent graded injection cylinder (2). The entire inner volume, from needle tip (7) to the front tip of the injection piston (1) will be filled with the liquid medication. Exit of the volume of liquid from the medication vial (9) is easily compensated for by an equal volume of air that enters the vial through the needle cannula (11) which acts as an air intake.

Once the required dose has been placed in the injection cylinder (2), the adaptor together with the vial can be unscrewed from the injection nozzle (6) and the pressure hypodermic syringe will be ready for use.

The path followed by the medication in the conventional version of the pressure hypodermic syringe is explained in FIG. 1. Before the medication vial (9) is placed on its holder (10) a needle (11) which will provide an air intake is passed through the vial's rubber lid (12). The rubber will also be pierced by the intake needle (7) whose lower tip is connected to an intake valve (13). This valve in turn contains a small ball (14) made of pliable material which allows the liquid to go down inside the syringe but prevents the dose already in the injection cylinder (2) from returning to the medication vial (9). This is achieved because, as the piston (1) starts moving forward, the very pressure exerted on the dose pushes the ball (14) against the base of the intake needle (7), thus sealing the passage.

On the other hand, when the injection piston (1) moves backward, the front orifice (5) of the injection nozzle (6) should be sealed against air intake to the injection cylinder (2) through that orifice (5). This requires a lid (15) and sealing disc (16) on the injection nozzle (6) to ensure that the inner space generated by the piston (1) being driven back will be filled only with the liquid suctioned from the medication vial (9) through the intake needle (7), the intake valve (13) and the internal intake channel.

Once the medication dose is inside the injection cylinder (2) the nozzle lid (15) may be removed from the injection nozzle (6) and the pressure hypodermic syringe will be ready to use.

What truly differentiates the present invention from any conventional hypodermic syringe is the extremely high pressure at which the injection piston (1) impels the medication at the moment of injection.

Such pressure is required because otherwise the dose coming out of the front orifice (5) as a jet would not be strong enough to pierce the skin.

In the common syringe the hypodermic needle performs this function. The piston may be depressed slowly by the applicator's thumb because in this case the piston is used solely to push the liquid through the hypodermic needle already lodged in intradermal, subcutaneous or intramuscular tissues.

With the pressure hypodermic syringe, a person would not be strong enough to manually push the piston so as to cause a liquid jet that would pierce the skin unaided. A storage mechanism is required with a given amount of mechanical power to be used all at once, that is, to push the injection piston (1) onto the dose stored inside the transparent injection cylinder (2).

Figure 3:
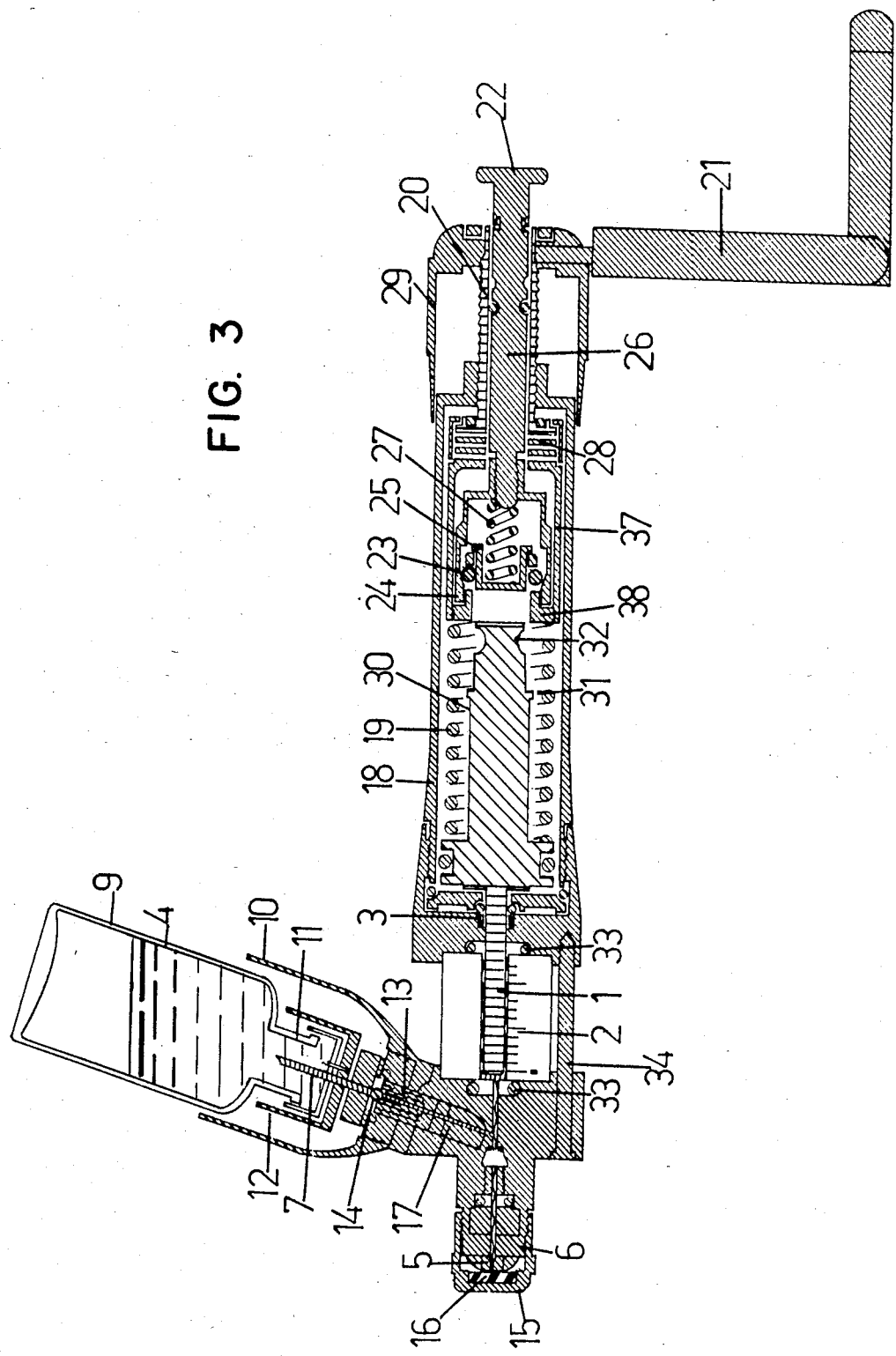
FIG. 3 (three) is a cross-section of the entire pressure hypodermic syringe showing the piston in the initial position on the scale, before the spring is compressed by the dose adjustment screw.

This mechanism is shown in detail in FIG. 3.

In addition to the front section described above, the pressure hypodermic syringe includes: a cylinder-shaped metal body (18) to house the injection piston driving mechanism; a spring (19) first compressed and when triggered, all its power will be used to propel the injection piston; a screw (20) which, when moving forward, will compress the spring against the injection piston (1), and when moving backward will pull back the injection piston (1), causing suction of the liquid and therefore dose adjustment; a handle (21) attached to the back end of the screw (20) to allow it to turn more easily during compression of spring (19); a coupling and uncoupling mechanism between the screw (20) and the injection piston (1) comprising a metal cylinder (37), a shot button (22), a ring-shaped support (38) with three or more orifices, three or more hardened metal balls (23), a metal ring-shaped bushing (24), a cylinder guide (25) keeping a plurality of balls (23) apart, a firing pin (26) with one end attached to the shot button (22) and the other connected to the metal bushing (24); a small spring (27) to move the cylinder guide (25) away from the firing pin (26), and two polished discs (28) to act as roller bearings and allow the dose adjustment screw (20) to be turned but not the coupling mechanism; and finally a cylinder drum (29) to protect the screw (20), sliding back and forth over the metal body (18) where a dosing scale may also be introduced.

The spring (19) compression procedure, aspiration of the desired dose into the transparent injection cylinder (2) and subsequent firing of the dose through the front orifice will be illustrated in sequence by FIGS. 3, 4, 5 and 6.

In FIG. 3 the pressure hypodermic syringe is seen in its initial position for use. The injection piston (1) is all the way forward with its front end facing the starting point (zero) of the dose scale on the transparent injection cylinder (2); the spring (19) is only slightly compressed between the coupling and uncoupling mechanism and the shoulder of the injection piston (1); the spring compression and dose adjustment screw (20) is threaded all the way back; the shot button (22) attached to the firing pin (26) and the metal bushing (24) are projected forward; the cylinder guide (25) is also projected forward to keep the balls (13) apart, and the nozzle lid (15) is properly screwed to prevent air intake through the front orifice (5).

As the handle (21) is turned clockwise, the screw (20) moves forward to push the coupling and uncoupling mechanism also forward; the latter then compresses the spring (19) against the back side of the injection piston (1).

The injection piston (1) has a metal shaft (30) attached with a cylindrical, semicircular groove (32) and shoulder (31) on its back section. When the coupling and uncoupling mechanism touches its front section to the shoulder (31) of the metal shaft (30), the handle (21) will stop turning clockwise, the screw (20) will be threaded fully forward and the spring (19) fully compressed.

Figure 4:
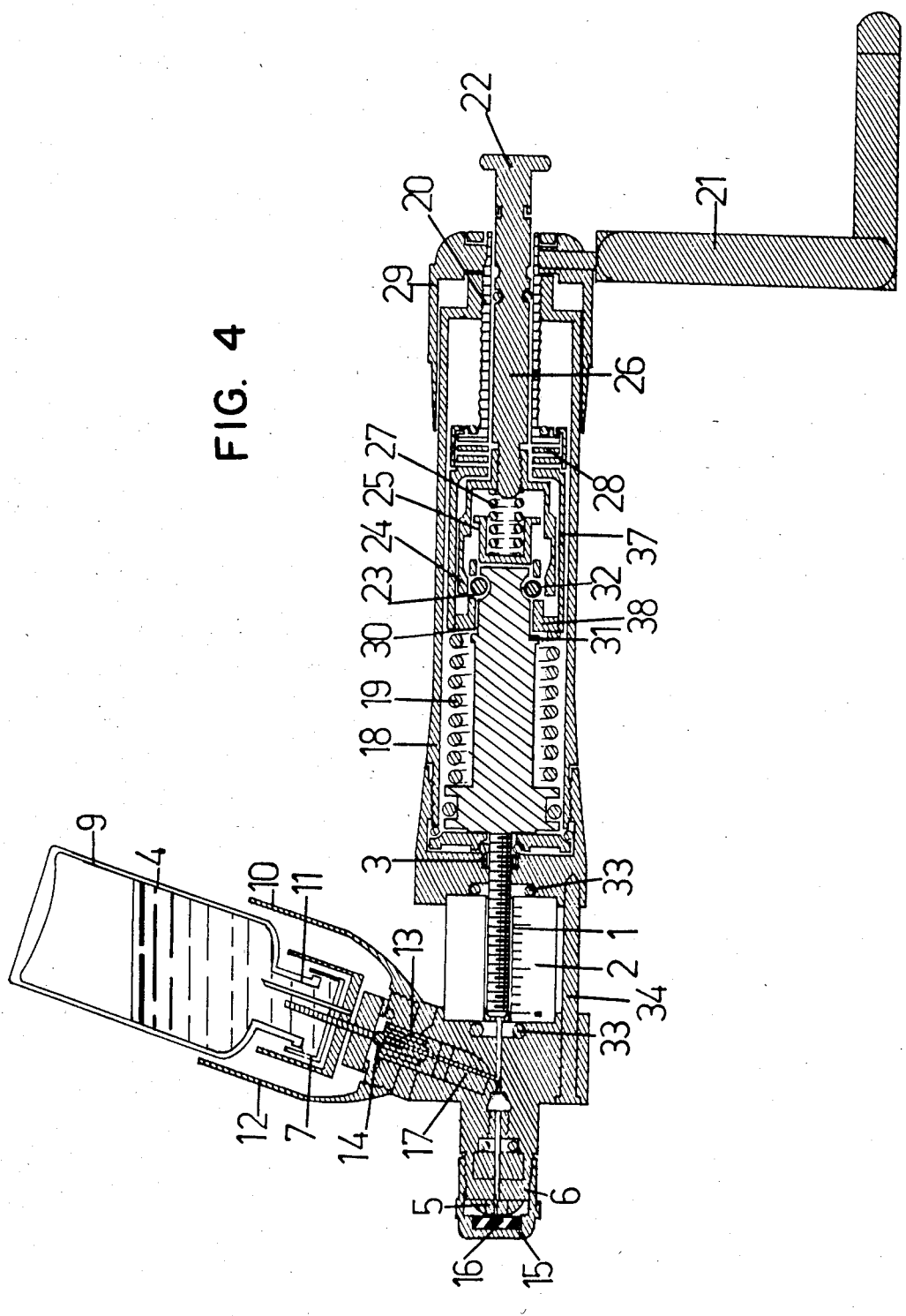
FIG. 4 (four) is a cross-section of the pressure hypodermic syringe with the spring compressed and the mechanical system set so the dose adjustment screw engages the injection piston to pull it backward.

This arrangement of the pressure hypodermic syringe is seen in FIG. 4.

The metal shaft (30) pushes back the cylinder guide (25) which presses on the small spring (27) which in turn also pushes back the metal bushing (24), the pin (26) and the shot button (22). The balls (23) are pushed into the groove (32) by the moving metal bushing (24). Since the balls (23) are prevented from falling out of the groove by the metal bushing (24) which remains fixed and blocks their exit, the spring (19) will stay compressed, and the injection piston (1) will form a single unit with the dose adjustment screw (20). That is, while the balls (23) stay in the groove (32), at the back section of the injection piston (1), any motion of the screw (20) will be followed by the entire piston, including its front end. If the handle (21) is turned counterclockwise, the screw (20) will move backward and pull the injection piston (1). So the screw (20) may be called a dose adjustment screw since the number of turns generated by the handle (21) will determine the volume of liquid suctioned into the transparent graded injection cylinder (2).

Figure 5:
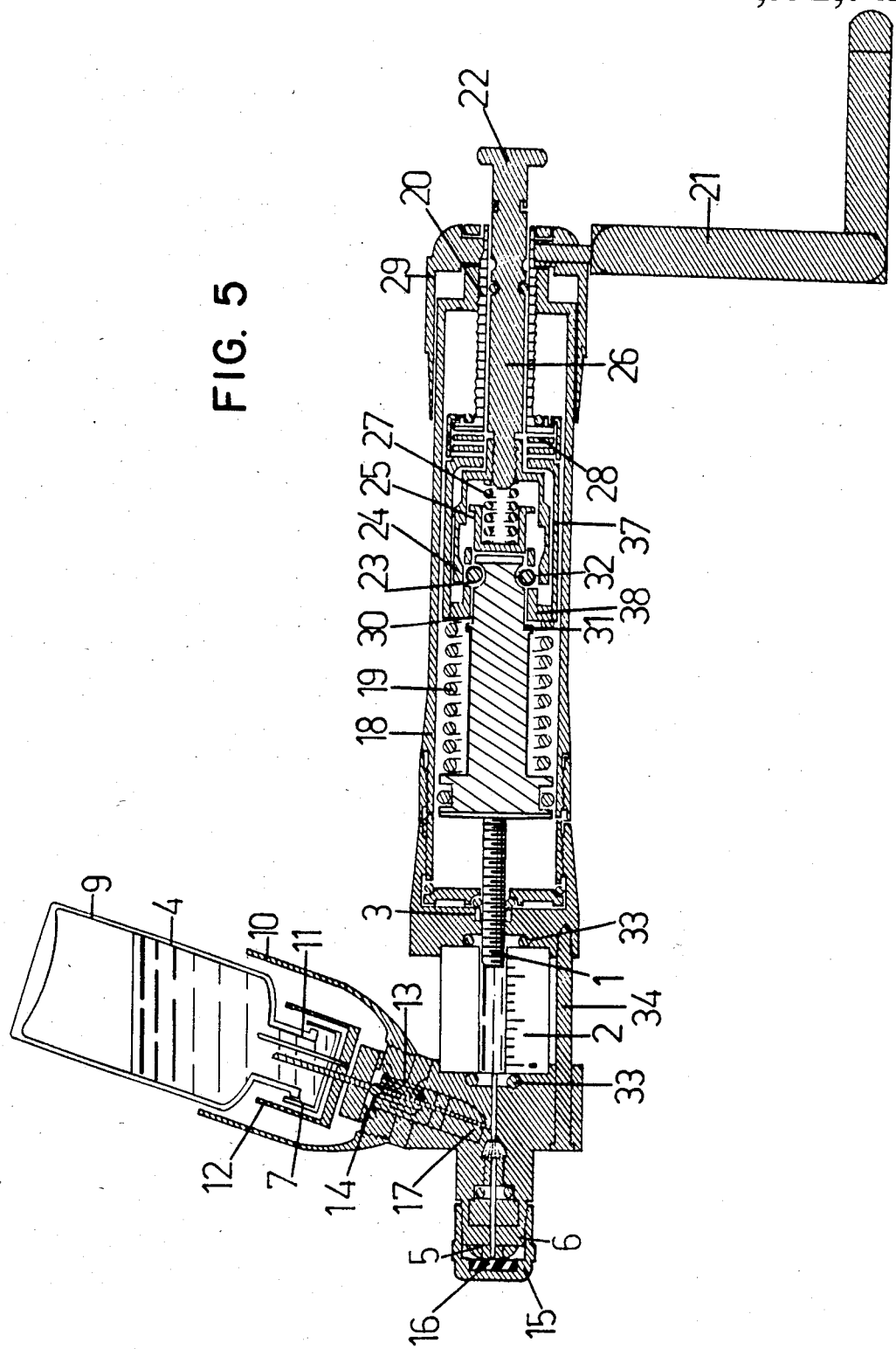
FIG. 5 (five) shows a cross-section of the pressure hypodermic syringe after the medication dose is suctioned inside the transparent graded injector cylinder.

FIG. 5 shows the dose adjustment screw (20) still coupled to the injection piston (1) after a given volume of liquid has been suctioned into the transparent graded injection cylinder (2).

In that position the pressure hypodermic syringe is ready for use. Now only the shot button (22) remains to be activated.

Uncoupling of the screw (20) from the injection piston (1) is as follows: As the shot button (22) is depressed, the metal bushing (24) will move forward. Thus the balls (23) inside the groove (32) will be expelled by the pressure generated by the compressed spring (19), which in turn will thrust the injection piston against the liquid located in the transparent cylinder (2), to expel the entire volume through the front orifice (5).

The balls (23) will stay inside their respective seats in the cylinder support (38) because as soon as the injection piston is released from the coupling and uncoupling mechanism the cylinder guide (25) is pushed by the small spring (27) and advances to the point where the shoulder had been (32).

Figure 6:
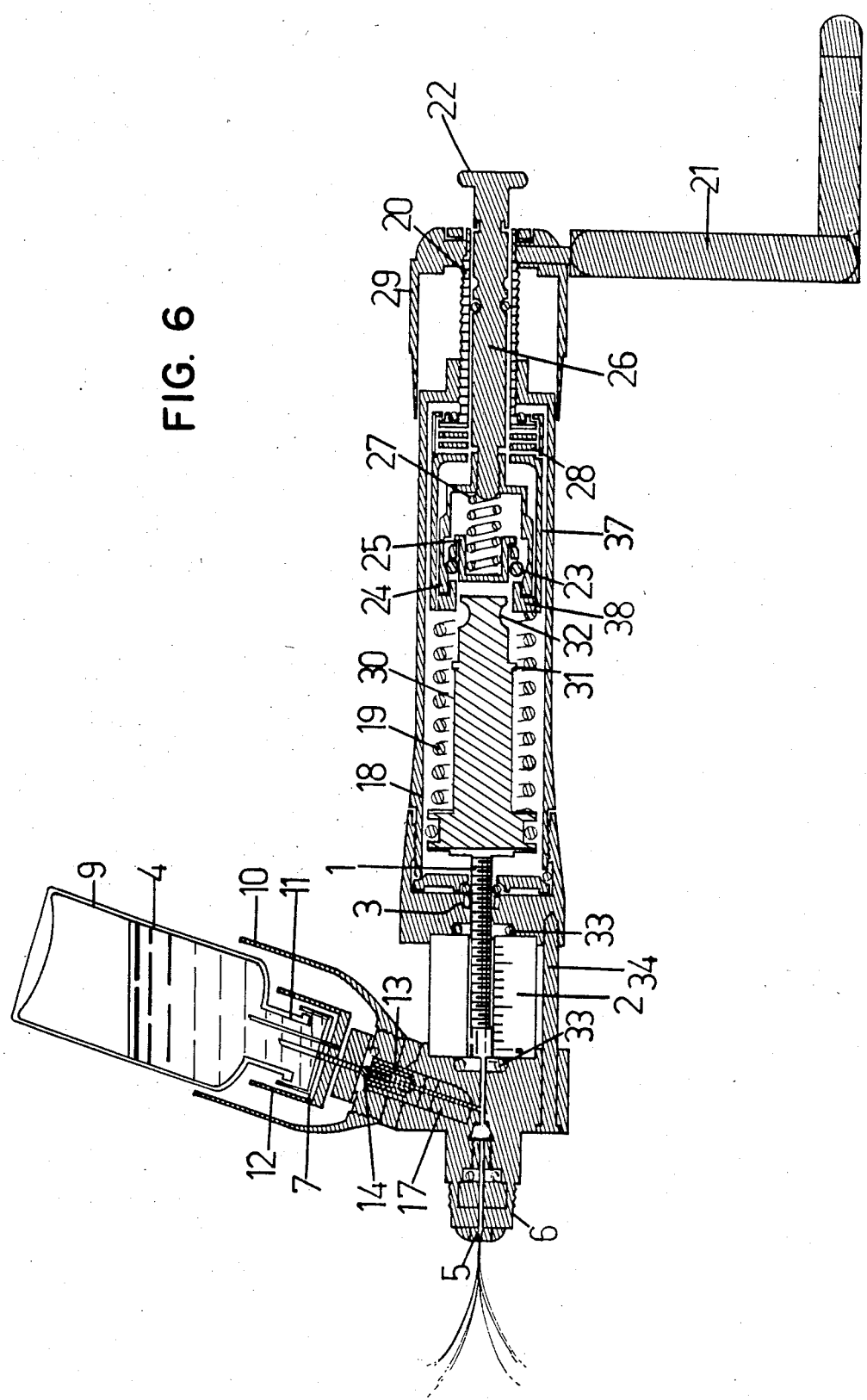
FIG. 6 (six) shows a cross-section of the pressure hypodermic syringe immediately after the shot button is depressed.

FIG. 6 shows the exact moment when the shot button (22) is depressed causing the screw (20) and piston (1) to uncouple and injecting the desired dose through the front orifice (5).

After injection, the pressure hypodermic syringe will return to the arrangement shown in FIG. 3, and the entire procedure may be started anew.

I claim:

1. A pressure hypodermic syringe for jet injection of variable doses of liquid medication in the intradermal, subcutaneous or intramuscular tissues of persons or animals, characterized by having a nozzle containing a minute front orifice through which the medication dose is expelled in jet form, an injection piston displaceable forward and backward respectively for aspiration and injection of the medication dose, a transparent graded cylinder to hold the desired dose each time and which can withstand the internal pressure generated as the piston presses the liquid toward the front orifice, sealing rings at both ends of said cylinder to prevent leakage of said liquid, said nozzle and front orifice forming a forward unit, said piston and spring comprising elements of a back unit, and one each of said sealing rings respectively tightly secured between the ends of said cylinder and said forward and back units, a spring which is depressed at a given pressure before each aspiration, and decompressed in a single movement, causing the piston to be promptly impelled forward to inject the medication dose through the front orifice, a screw which, when turned forward, causes the spring to compress, and when turned backward becomes coupled to the back end of the piston, pulling it backward and causing aspiration of the medication dose into the transparent graded cylinder, and a shot button that when activated uncouples the back end of the piston from the screw, causing sudden decompression of the spring which in turn forces the piston to impel the medication dose toward the front orifice, such that the syringe comprising all the above components can simultaneously inject variable doses of the medication dispensed in jet form, while allowing for visual dose adjustment at each aspiration through the changing of the position of the forward face of the piston as it is displaced inside the transparent graded cylinder, thereby allowing the user to visualize at once and each time the entire graded scale, the entire medication dose inside the cylinder, and the front end of the piston.

2. A pressure hypodermic syringe according to claim 1, including at least two screws extending between said forward and back unit to retain said cylinder sandwiched therebetween, said screws disposed parallel to the central longitudinal axis of said cylinder and when tightened causing said units to compress said two sealing rings respectively against both ends of said cylinder.

3. A pressure hypodermic syringe according to claim 1, characterized by having a high pressure sealing ring between said cylinder and injection piston surrounding said piston to the rear of said transparent graded cylinder both when said injection piston is displaced forward or backward respectively for aspiration and injection of the liquid medication, said high pressure sealing ring always remaining fixed at a set point relative said graded cylinder thereby requiring only the surface of said piston to be polished and eliminating the need for the internal diameter of said transparent graded cylinder to be likewise polished.

4. A pressure hypodermic syringe according to claim 1 wherein said forward unit includes a holder for a medication vial and intake needle, wherein one end of said needle is inserted in said vial and the other end is coupled to a valve also located in said forward unit, said valve adapted to open automatically by suction created by said injection piston as the latter starts its backward motion causing aspiration of the liquid, and said valve also closing automatically through the compression of the liquid when the liquid is pushed forward by the injection motion of said piston.

5. A pressure hypodermic syringe according to claim 1, including an adaptor coupled to the syringe only during liquid aspiration from a vial provided with an intake needle, said adaptor containing at one end an internal groove provided with a sealing ring resting over said nozzle adjacent said front orifice in such a way that the entire path from said intake needle to said transparent injection cylinder is tightly sealed to allow the medication to be aspired through suction of said injection piston and to pass through said intake needle and said front orifice of said nozzle before entering said transparent injection cylinder.

6. A pressure hypodermic syringe according to claim 1 including coupling means between said injection piston and said screw for dose adjustment, said coupling means including a metal shaft containing an indented groove and fixed to the back end of said piston, a metal cylinder fixed to said screw and containing an internal ring-shaped support having at least three holes arranged around its diameter, a plurality of balls made of hardened material adapted to be urged inside toward the central longitudinal axis of the syringe by a ring-shaped metal bushing, in turn pushed backward by said shaft coupled to said piston when said screw is turned fully forward, so that as said metal bushing pushes said balls inward the latter fall into said groove of said shaft thereby coupling said piston to said screw.

7. A pressure hypodermic syringe according to claim 6, whereby said spring when compressed by the screw with said injection piston fully stopped at the forward most position, insures that when liquid is aspired into said transparent cylinder, said spring is already compressed and the screw coupled to the injection piston thereby forming a single unit comprising the piston, the compressed spring, and screw in a way such that as the screw is turned backward the entire said unit is pulled backward, including the front end of the piston, through which the dose aspirated into the transparent graded cylinder can be read.

8. A pressure hypodermic syringe for jet injection of variable doses of liquid medication in the intradermal, subcutaneous or intramuscular tissues of persons or animals, comprising: a forward unit including a nozzle containing a minute front orifice through which the medication dose is expelled in jet form, said forward unit provided with a holder for a medication vial and an intake needle with one end insertable in said vial and the other end coupled to a valve also located in the forward unit, a transparent injection cylinder rearwardly of said nozzle, an injection piston displaceable backward and forward out of and into said transparent injection cylinder respectively for aspiration and injection of the medication dose, a spring compressed at a given pressure before each aspiration, said valve opening automatically by suction created as said injection piston starts its backward motion causing aspiration of the liquid, means operable to suddenly decompress said compressed spring to promptly impel said piston forward to inject the medication dose within said transparent injection cylinder through said front orifice, and said valve closing automatically as a result of the compression of the liquid when the latter is pushed forward by the injection motion of said piston.

9. A pressure hypodermic syringe according to claim 8, including a high-pressure sealing ring between said cylinder and said injection piston, surrounding the latter rearwardly of the back end of said transparent injection cylinder, said sealing ring remaining fixed relative said cylinder even when the injection piston is displaced backward or forward respectively for aspiration and injection of a liquid.

* * * * *